United States Patent
Davis et al.

[11] Patent Number: 5,882,197
[45] Date of Patent: Mar. 16, 1999

[54] ILLUMINATED SUCTION TOOL WITH DISPOSABLE TIP

[76] Inventors: Warren Davis, 942 Eldorado La., Las Vegas, Nev. 89123; David Wasserman, 2095 Mohigan Way, Las Vegas, Nev. 89109; Robert Dybus, 1437 Rawhide Rd., Boulder City, Nev. 89005

[21] Appl. No.: 903,757

[22] Filed: Jul. 31, 1997

Related U.S. Application Data

[63] Continuation of Ser. No. 562,730, Nov. 27, 1995, abandoned.

[51] Int. Cl.[6] .................................................. A61C 17/00
[52] U.S. Cl. ................................................. 433/91; 433/29
[58] Field of Search .................................. 433/29, 31, 88, 433/91, 95, 80, 96, 93, 94; 604/902, 119; 239/33; 222/566, 569

[56] References Cited

U.S. PATENT DOCUMENTS

| | | | |
|---|---|---|---|
| 2,022,927 | 12/1935 | Simpson | 433/91 |
| 4,451,257 | 5/1984 | Atchley | 604/902 |
| 4,538,631 | 9/1985 | Prince | 433/91 |
| 4,872,837 | 10/1989 | Issalene et al. | 433/29 |
| 4,966,551 | 10/1990 | Betush | 433/95 |
| 5,123,840 | 6/1992 | Nates | 433/91 |

FOREIGN PATENT DOCUMENTS

| | | | |
|---|---|---|---|
| 3939859 | 6/1991 | Germany | 433/91 |
| 8606613 | 11/1986 | WIPO | 433/91 |

*Primary Examiner*—Cary E. O'Connor
*Attorney, Agent, or Firm*—John Edward Roethel

[57] ABSTRACT

A dental suction tool has a disposable sanitary plastic suction tip to prevent cross contamination from one patient to the next. The suction tip is formed as a generally cylindrical hollow tubing and made of disposable plastic material. One end of the suction tip has at least one beveled section along an outer wall surface of the suction tip so that the suction tip can be properly aligned in the dental suction tool. Alternatively, one end of the suction tip has at least one recess that is adapted to cooperate with a keying element in the dental suction tool to properly align the suction tip in the dental suction tool.

16 Claims, 11 Drawing Sheets

ILLUMINATED SUCTION TOOL WITH DISPOSABLE TIP

This is a continuation of Application Ser. No. 08/562,730, filed Nov. 27, 1995, now abandoned.

BACKGROUND OF THE INVENTION

The present invention was developed to add further function to the widely accepted evacuation systems currently used for suction or aspiration. The concept of suction or aspiration in the dental office has its roots in the old fashioned spittoon. The spittoon was later replaced by the gravity flow cuspidor, then by the flush cup and finally by the suction tip/aspirator tip/vacuum tip which are interchangeable terms varying by the user and based on the size of the aperture in the device.

These dental suction instruments are used by dentists to remove fluids and other foreign objects that accrue in the patient's oral cavity during typical dental procedures. The conventional dental suction tool comprises a suction tip connected by a long tubing to a vacuum source. The dental suction tool can be configured to hang in the corner of the patient's mouth or is manipulated by the dentist to suction the oral cavity.

With the rising incidence of communicable diseases such as hepatitis and acquired immune deficiency syndrome, extreme care must be taken to prevent the transmission of germs (viral or bacteria) from one patient to the next. With the conventional suction devices, it is necessary to sterilize at least the tip of the suction device after each patient use. During the use of the suction device, water, saliva and blood from the patient's mouth is drawn into the tip for removal from the oral cavity. If cleaning and sterilization is not effected, it would be very easy to transfer infection from one patient to the next. Also, latent bacterial growth can be promoted in both the tip and the entire vacuum suction system lines because of the existence of this potentially contaminating material. To further mitigate this possibility of cross-contamination from one patient to the next, the routine sterilization of suction tips is desirable.

It is desirable to also supply light into the oral cavity to assist the dentist in performing necessary dental procedures. Most dental operatories have an overhead task lighting system with reflective surfaces that help concentrate the light on the patient's mouth. However, the dentist will often stand in the path of the light which minimizes the effectiveness of the overhead light. One of the major nuisances and frustrations in the practice of dentistry is the constant need for the dentist to spend time adjusting the direction of this overhead lighting.

Various dental tools have been provided with a light source to assist the dentist during various dental activities. For example, a typical dental drill will include a fiberoptic bundle that transmits light from a light source to the end of the dental drill which allows the dentist to provide light directly to the area in which the drilling is occurring. Representative of this technology are the disclosures shown in U.S. Pat. No. 4,507,085 (Mosimann) and U.S. Pat. No. 5,088,924 (Woodward).

Dental syringe tip handpieces have also been provided with a light source to illuminate the area into which the air and/or water are to be sprayed. Representative of these devices is the disclosure of U.S. Pat. No. 4,619,612 (Weber) which shows a fiberoptic bundle disposed down the center of a metal syringe tip assembly. A light bulb acts as the light source and is disposed in the interior of the handpiece. The syringe tip used in the disclosure of the Weber patent is a metal, non-disposable syringe tip which must be autoclaved prior to use on the next patient.

Previous attempts to use light in conjunction with a suction tip were done by running a fiberoptic bundle tangent and parallel to the suction tip. The optical conduit for the fiberoptic bundle was fixed to the suction tip by a series of clamps along the length of the suction tip. However, the results from this configuration were less than desirable for several reasons.

The fiberoptic bundles that were attached to the suction tips still needed to be sterilized before being used on the next patient. Fiberoptic bundles are not particularly amenable to the heat of sterilization and the expense and inconvenience of frequent replacement of these fiberoptic bundles can be prohibitive. It is also necessary to clean up the areas on the suction tip at which the clamps are attached and this can be quite cumbersome and time consuming. Another problem with this fiberoptic bundle configuration is that the light is positioned off-center from the suction tip so that the light being transmitted into the oral cavity of the patient still casts shadows from the suction tip, itself, which can do more harm than good.

The novel concept developed herein is to transmit light to the field of operation by transmitting a light source through a transparent plastic material which simultaneously serves as the suction tip of the dental suction device. The fact that the light is centered relative to the suction tip minimizes any shadows in the oral cavity and reduces the need for the dentist to rely on his overhead task lighting, which is constantly in need of adjustment.

It is proposed that the use of the present invention in conjunction with the light source that is coupled to the air/water syringe tip will provide sufficient light in the patient's oral cavity to obviate the need for the overhead task lighting and eliminate the time spent constantly adjusting this task lighting.

It is an object of the present invention to provide a disposable suction tip as part of the dental suction tool so that each patient can receive a clean and uncontaminated suction tip.

It is a feature of the present invention that the suction tip portion of a dental suction tool is made from a disposable plastic material.

It is an advantage of the present invention that cross-contamination between patients due to improperly cleaned or sterilized suction tips is eliminated because each patient is provided with a new, clean and uncontaminated suction tip that is only used on that patient.

It is a further object of the present invention to provide a useful source of light that can be transmitted into the oral cavity of the patient whenever the dentist is using a dental suction tool.

It is a further feature of the present invention to provide a light source at one end of the suction tip on the interior of the adaptor that holds the suction tip in the dental tool. Light from the light source is directed into one end of the suction tip and carried along the length thereof. At the opposite end of the suction tip, the light radiates from the suction tip and can be used to illuminate the oral cavity of the patient.

It is a further advantage of the present invention that a dentist will be able to illuminate the oral cavity using the same instrument that he is using to suction liquids and other foreign matter from the oral cavity of the patient. Any dental procedures that require use of the dental suction tool will be more easily, safely and effectively carried out because the dentist will be able to see exactly where in the oral cavity he is working.

It is a further object of the present invention to provide means for properly aligning the suction tip in the dental suction tool.

It is a further feature of the present invention to provide at one end of the suction tip at least one beveled section along an outer wall surface of the suction tip so that the suction tip can be properly aligned in the dental suction tool. Alternatively, one end of the suction tip is provided with at least one recess that is adapted to cooperate with a keying element in the dental suction tool to properly align the suction tip in the dental suction tool.

It is a further advantage of the present invention that a dentist will be able to properly align the suction tip in the dental suction tool.

Other objects, features and advantages of the present invention will become apparent from a consideration of the following detailed description.

SUMMARY OF THE INVENTION

A dental suction tool has a disposable sanitary plastic suction tip to prevent cross contamination from one patient to the next. The suction tip is formed as a generally cylindrical hollow tubing and made of disposable plastic material. One end of the suction tip has at least one beveled section along an outer wall surface of the suction tip so that the suction tip can be properly aligned in the dental suction tool. Alternatively, one end of the suction tip has at least one recess that is adapted to cooperate with a keying element in the dental suction tool to properly align the suction tip in the dental suction tool. Additionally, a light source such a fiberoptic bundle and a ring light are provided on the interior of the dental suction tool to provide light to the end of the plastic disposable suction tip. Illumination from the ring light is transmitted along the length of the suction tip and is emitted from the end thereof to illuminate the oral cavity during dental procedures.

DETAILED DESCRIPTION OF THE PREFERRED EMBODIMENTS

Figure 1:
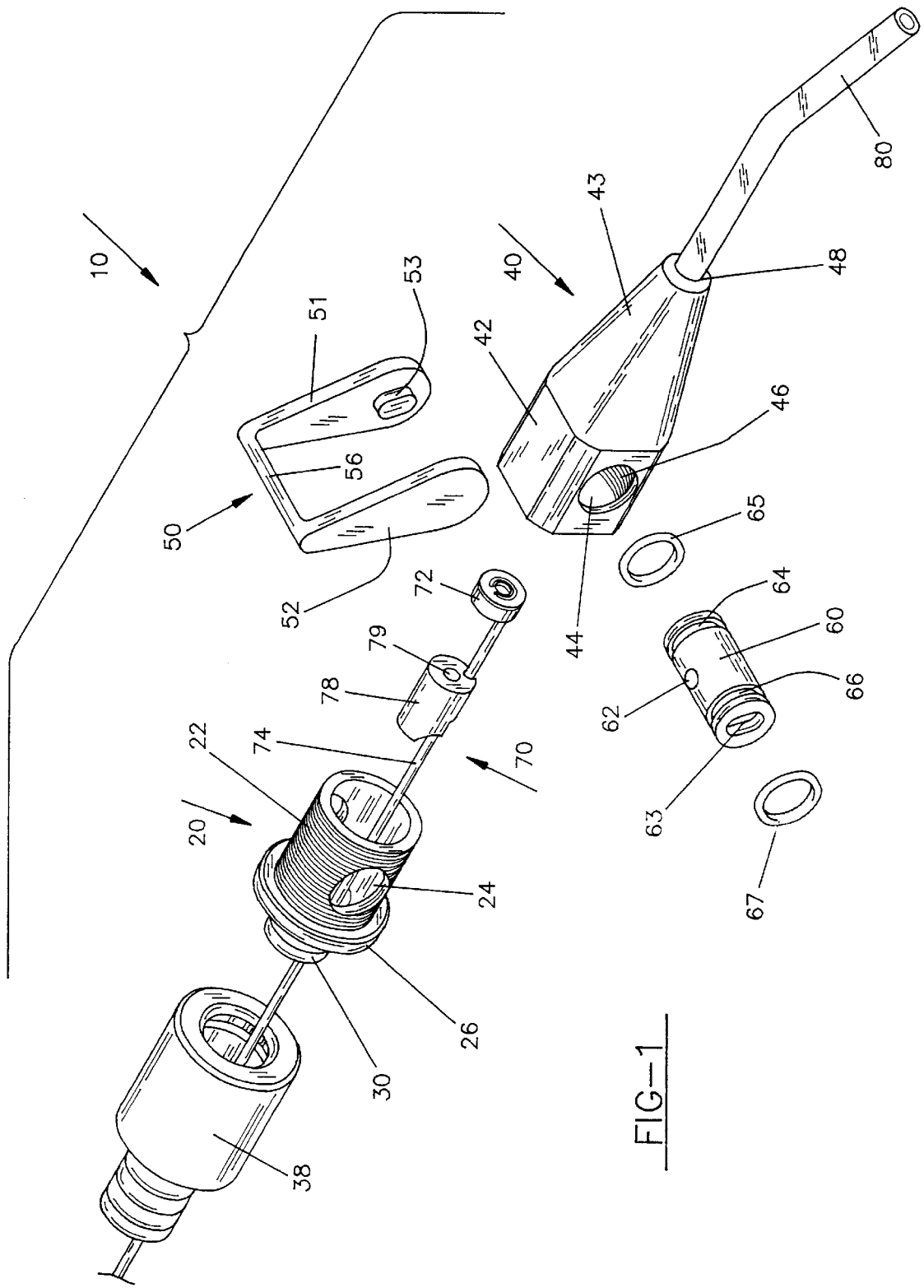
FIG. 1 shows an isometric exploded view of the dental suction tool of the present invention.

The dental suction tool of the present invention is shown generally at 10 in FIG. 1. The dental suction tool 10 comprises a valve cap 20, a valve body 40, a lever 50 and a light assembly 70. A suction tip 80 is mounted in the valve body 40 and the entire dental suction tool 10 is connected to a source of vacuum and electrical power (not shown).

The valve cap 20 comprises an externally threaded cap section 22, preferably configured as a hollow cylinder. On each of the diametrically opposite sides of the threaded cap section 22, a cylinder aperture 24 is provided of sufficient diameter to receive the rotating cylinder 60 therethrough when the dental suction tool 10 is assembled. Toward the rear of the threaded cap section 22, there is provided a cap top 26 and a cap extension 30. The cap extension 30 is provided with an annular groove 32 to receive the tubing connector base 38. The tubing connector base 38 is attached to the tubing (not shown) that runs from the power supply and the vacuum suction supply typically provided at a remote location from the dentist's chair.

The valve body 40 includes a generally hollow threaded body section 42 with a set of internal threads 46 that cooperate and receive the threaded cap section 22 of the valve cap 20 when the valve cap 20 is assembled with the valve body 40. The valve body 40 has a cylinder aperture 44 on its one side and another cylinder aperture (not shown) on the opposite side of the threaded body section 42. These cylinder apertures receive the rotating cylinder 60 when the dental suction tool 10 is assembled.

The rotating cylinder 60 is a generally cylindrical body with a cylinder passageway 62 diametrically therethrough. Each end of the rotating cylinder 60 has a fastening recess shaped to correspond to the fastening pins on the lever 50. One end of the rotating cylinder 60 has an annular groove 66 that receives an O ring 67 and the other end of the rotating cylinder 60 has a like annular groove 64 that receives an O ring 65.

The lever 50 can be of any suitable configuration such as the generally U-shaped configuration shown. The lever 50 has a first side arm 51 with a first fastening connector 53 mounted thereon that fits in the associated first fastening recess (not shown) on the rotating cylinder 60 and a second side arm 52 with a second fastening connector (not shown) that fits in the associated second fastening recess 63 on the rotating cylinder 60. Each of the first side arm 51 and the second side arm 52 are connected by the cross piece 56 so that each arm moves with the other to rotate the rotating cylinder 60 upon movement of the lever 50.

The dental suction tool 10 also includes a light assembly 70 comprising a light ring 72 at one end of a fiberoptic bundle 74 that extends the length of the dental suction tool 10. Adjacent, but slightly separated from the light ring 72 is an alignment cylinder 78 which assists in properly aligning the light assembly 70 on the interior of the dental suction tool 10 when all of the elements of the dental suction tool 10 are assembled together into its working state.

The valve body 40 includes a suction tip passageway 48 which opens at the end of the conical end section 43 in which is inserted the disposable suction tip 80. The suction tip 80 may have a number of configurations as will be further explained herein.

Figure 2:
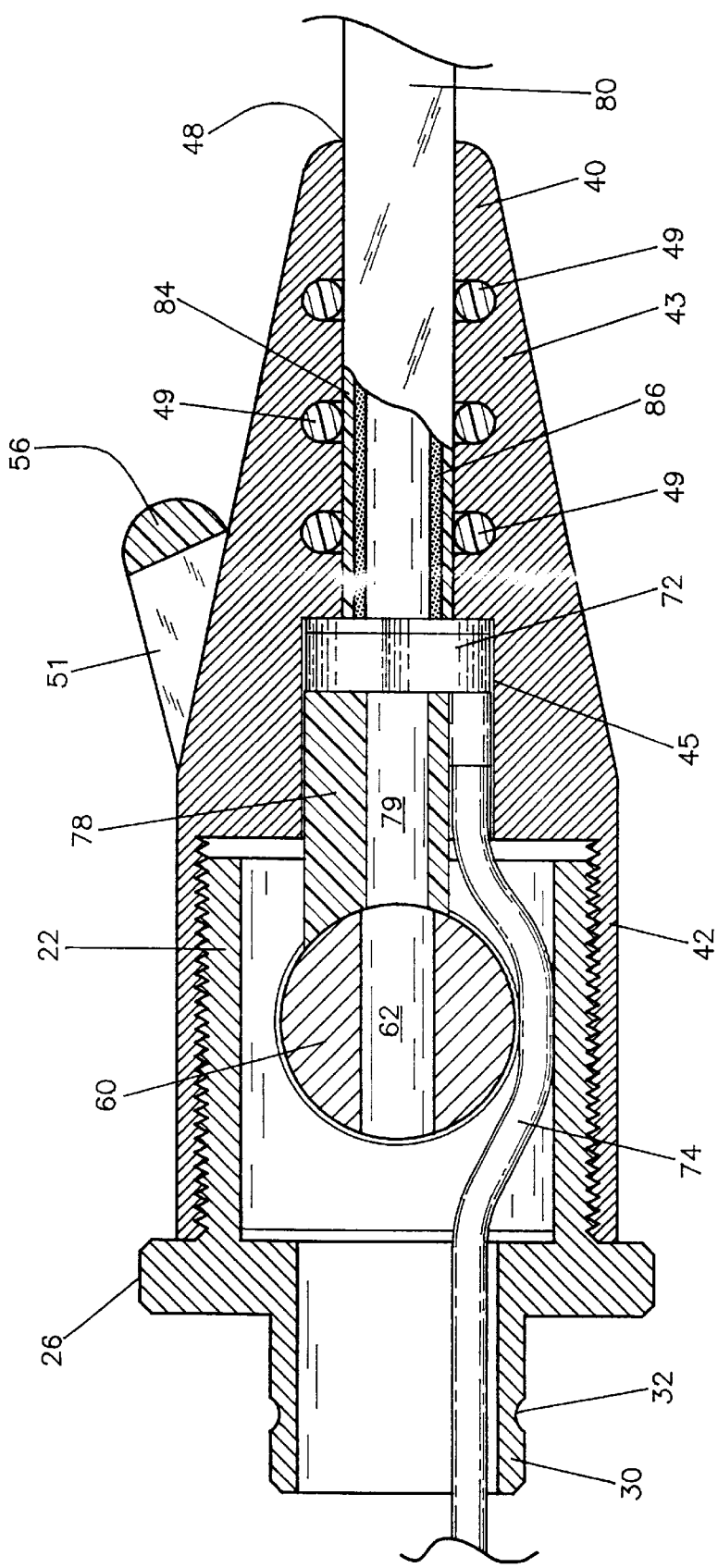
FIG. 2 is a cross sectional view of one embodiment of the dental suction tool of the present invention with the suction valve in the open position.

FIG. 2 shows in cross section the dental suction tool 10 in an assembled condition with the lever 50 set so that the rotating cylinder 60 is open to allow the vacuum source to provide suction to the suction tip 80. The valve body 40 has a light ring cavity 45 that receives the light ring 72 and the alignment cylinder 78. When the suction tip 80 is inserted into the suction tip passageway 48 of the valve body 40, the end of the suction tip 80 abuts the light ring 72. The suction tip 80 is held securely inside the valve body 40 by means of one or more O rings 49 provided therein along the length of the suction tip passageway 48. By simply pulling out the suction tip 80, a new suction tip 80 can be inserted into the valve body 40 for each new patient thereby maintaining a clean and sanitary suction tool and the elimination of any possible cross contamination between patients.

Activation of the power supply to the light assembly 70 transmits light through the fiberoptic bundle 74 and into the light ring 72. The light emitting from the light ring 72 is transmitted along the length of the suction tip 80 and out the end thereof into the patient's oral cavity.

In the embodiment of the invention shown in FIG. 2, the suction tip 80 is a bi-layered extrusion. The inner layer is a fiberoptic tubing 86 which will transmit the light from the light ring 72 along the length of the fiberoptic tubing 86 and out its end into the patient's mouth. The outer layer is plastic layer 84 which can be clear or opaque as desired. In the preferred embodiment, the plastic layer 84 should be a clear light-transmitting plastic material which can also transmit light from the light ring 72 along the length of the plastic layer 84.

Figure 3:
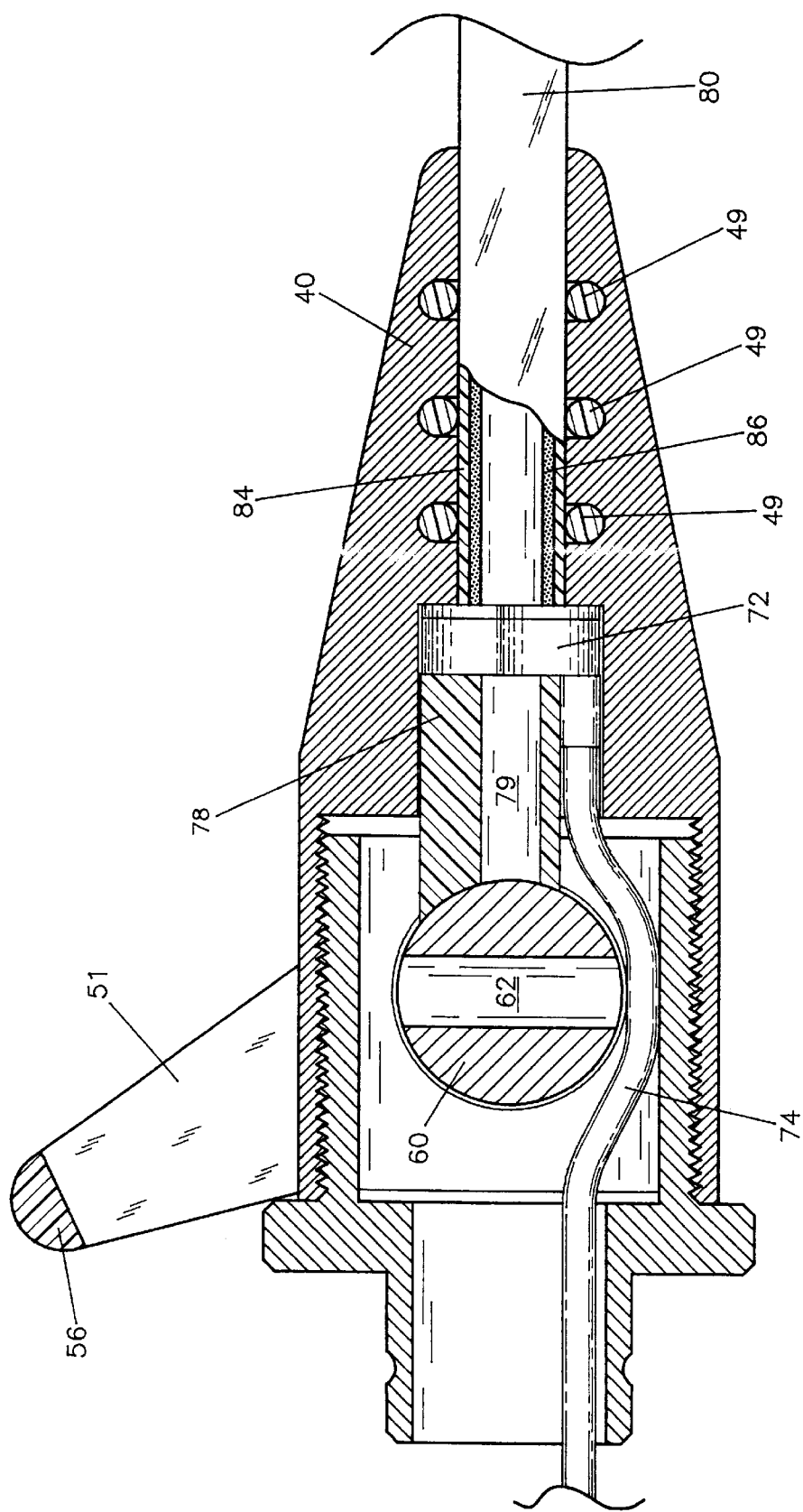
FIG. 3 is a cross sectional view of the dental suction tool of the present invention with the suction valve in the closed position.

When the lever 50 is rotated approximately 90° as shown in FIG. 3, the rotating cylinder 60 likewise rotates approximately 90°. This disassociates the cylinder passageway 62 from the alignment cylinder passageway 79 and no suction will be provided to the suction tip 80. However, light from the light ring 72 will continue to be transmitted along the length of the suction tip 80 and into the patient's oral cavity as long as power is supplied to the fiberoptic bundle 74. This allows the dental suction tool 10 to function as a light source even when suction is not required for a particular dental procedure.

Figure 4:
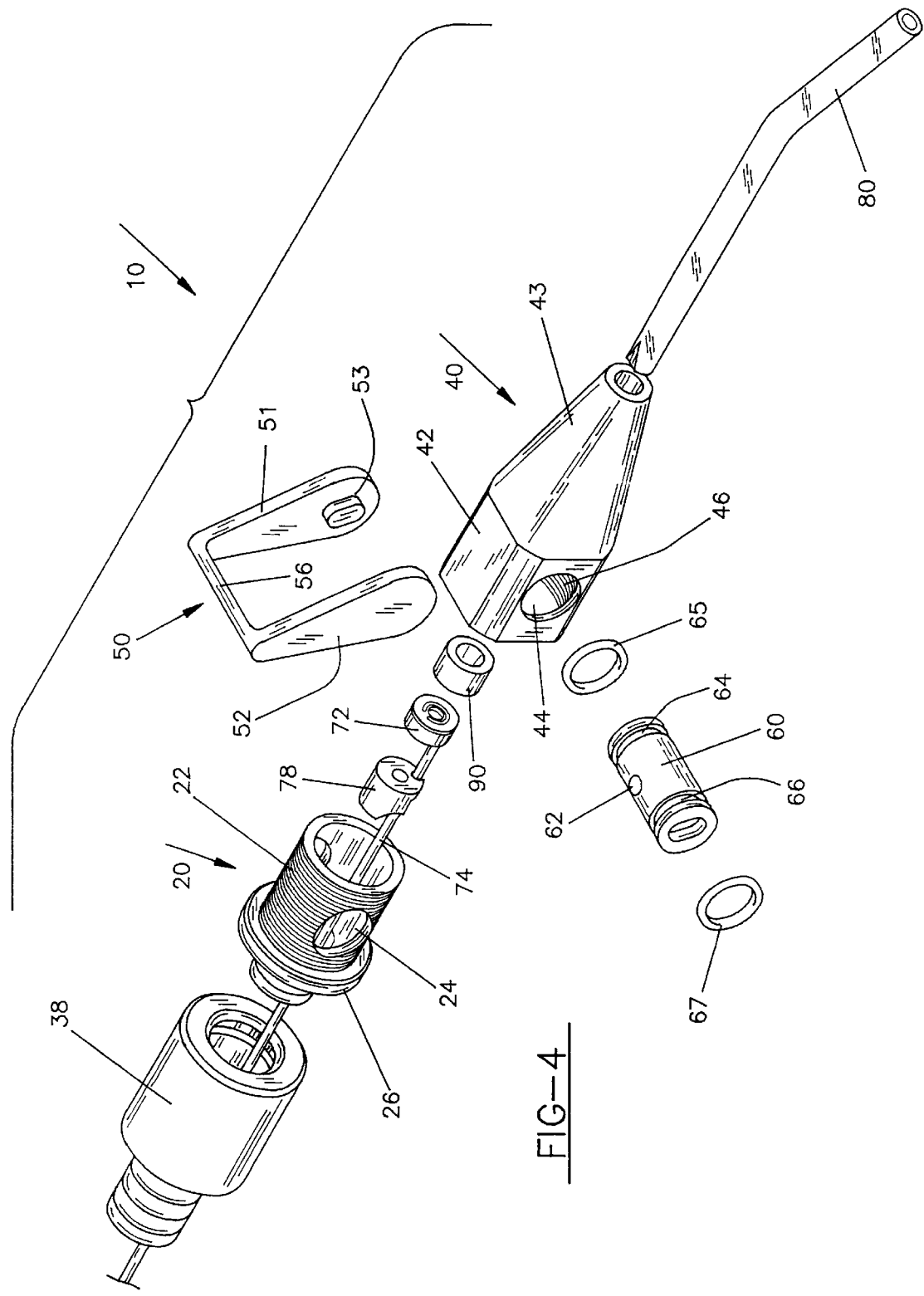
FIG. 4 shows an isometric exploded view of a modified dental suction tool of the present invention.
Figure 5:
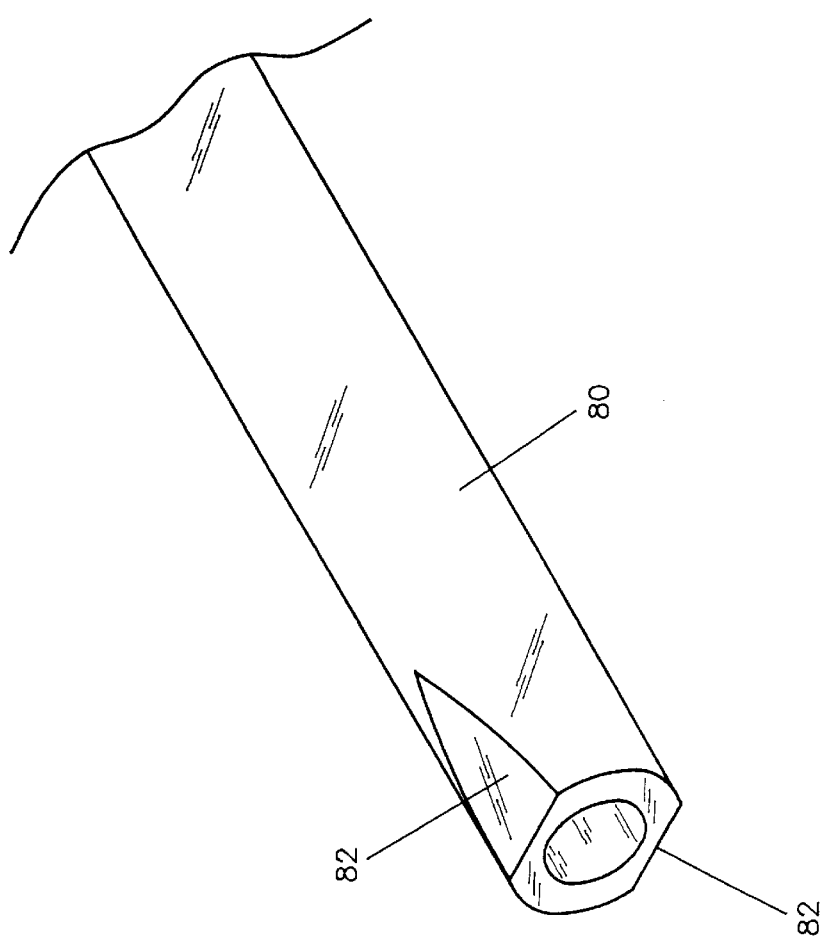
FIG. 5 shows an isometric view of a modified suction tip of the present invention.
Figure 6:
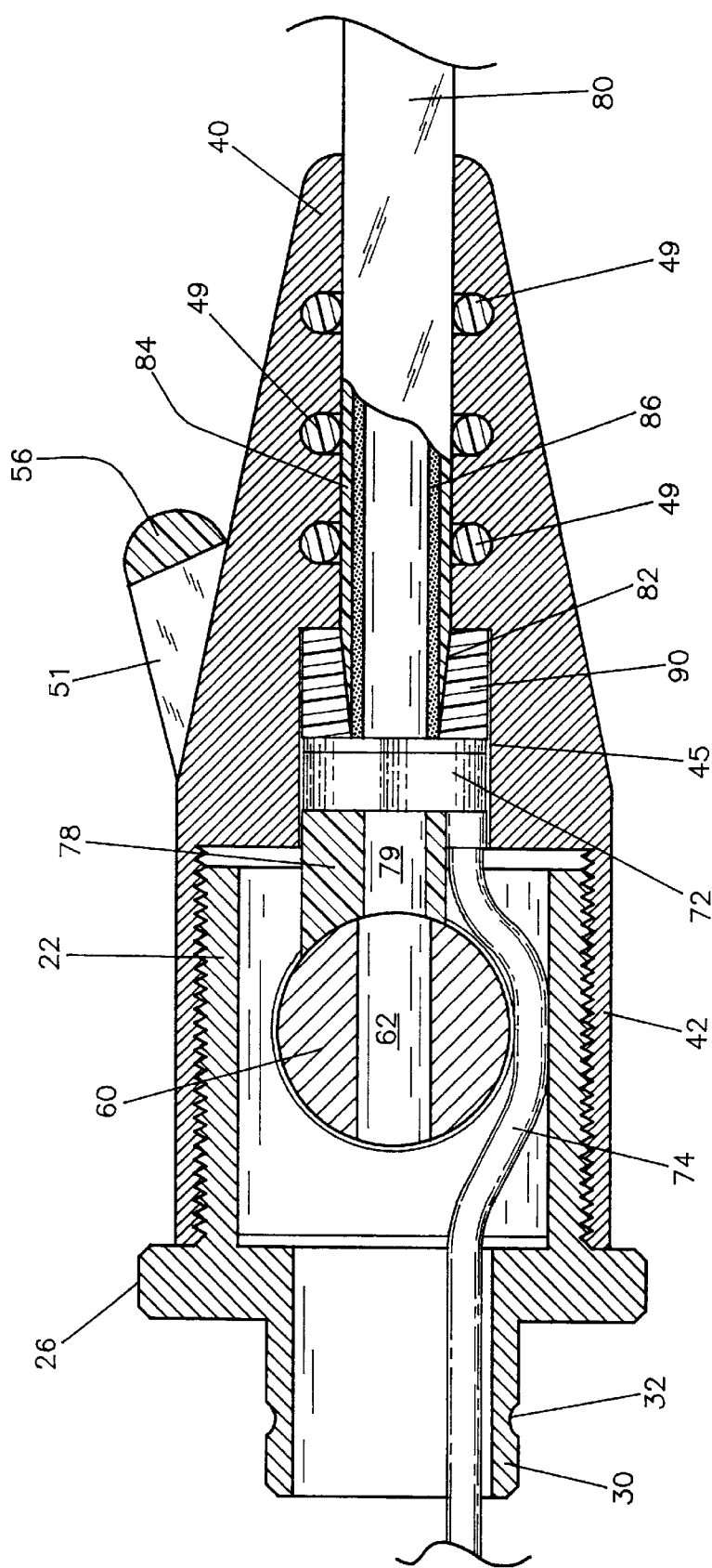
FIG. 6 is a cross sectional view of the modified dental suction tool shown in FIG. 4 with the suction valve in the open position.

FIGS. 4–6 show a modification of the dental suction tool 10 of the present invention. Like reference numerals are used to identify the elements from FIGS. 1–3 that are the same in FIGS. 4–6.

In FIGS. 4 and 6, a tip insertion block 90 is added to the rear cavity 45 in front of the light ring 72. As shown in FIGS. 5 and 6, the tip insertion block 90 has beveled top and bottom portions on its internal bore that correspond to the beveled sections 82 on diametrically opposed sides in the outer wall surface of the suction tip 80. In the preferred embodiment of the present invention as shown in FIG. 5, the beveled sections 82 are formed in the outer wall surface of the suction tip 80. As the suction tip 80 is inserted into the valve body 40, the beveled sections 82 align with the beveled top and bottom portions on the interior of the tip insertion block 90 and effect the proper alignment of the suction tip 80 in the valve body 40.

Figure 7:
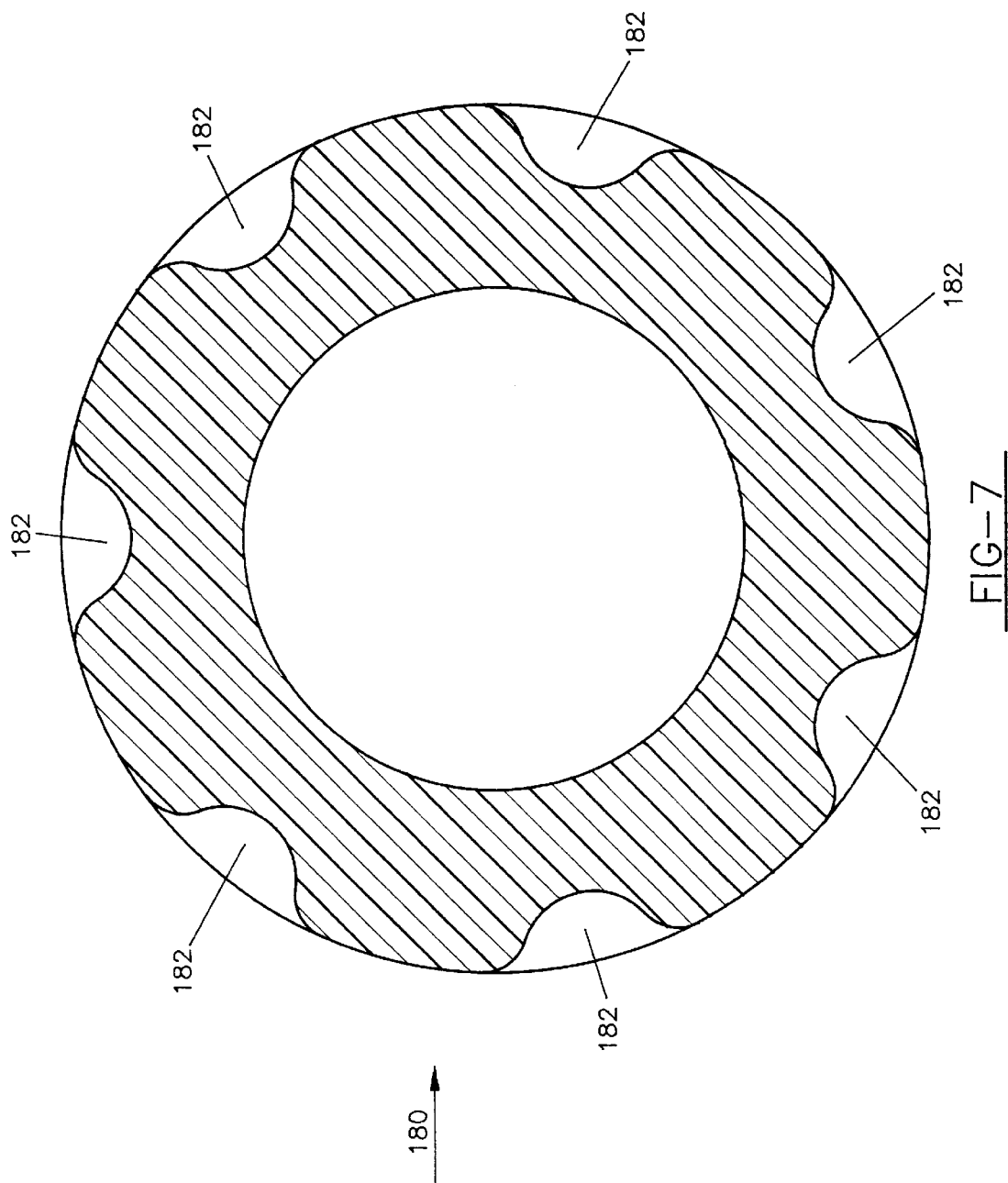
FIG. 7 shows an end view of another modified suction tip of the present invention.
Figure 8:
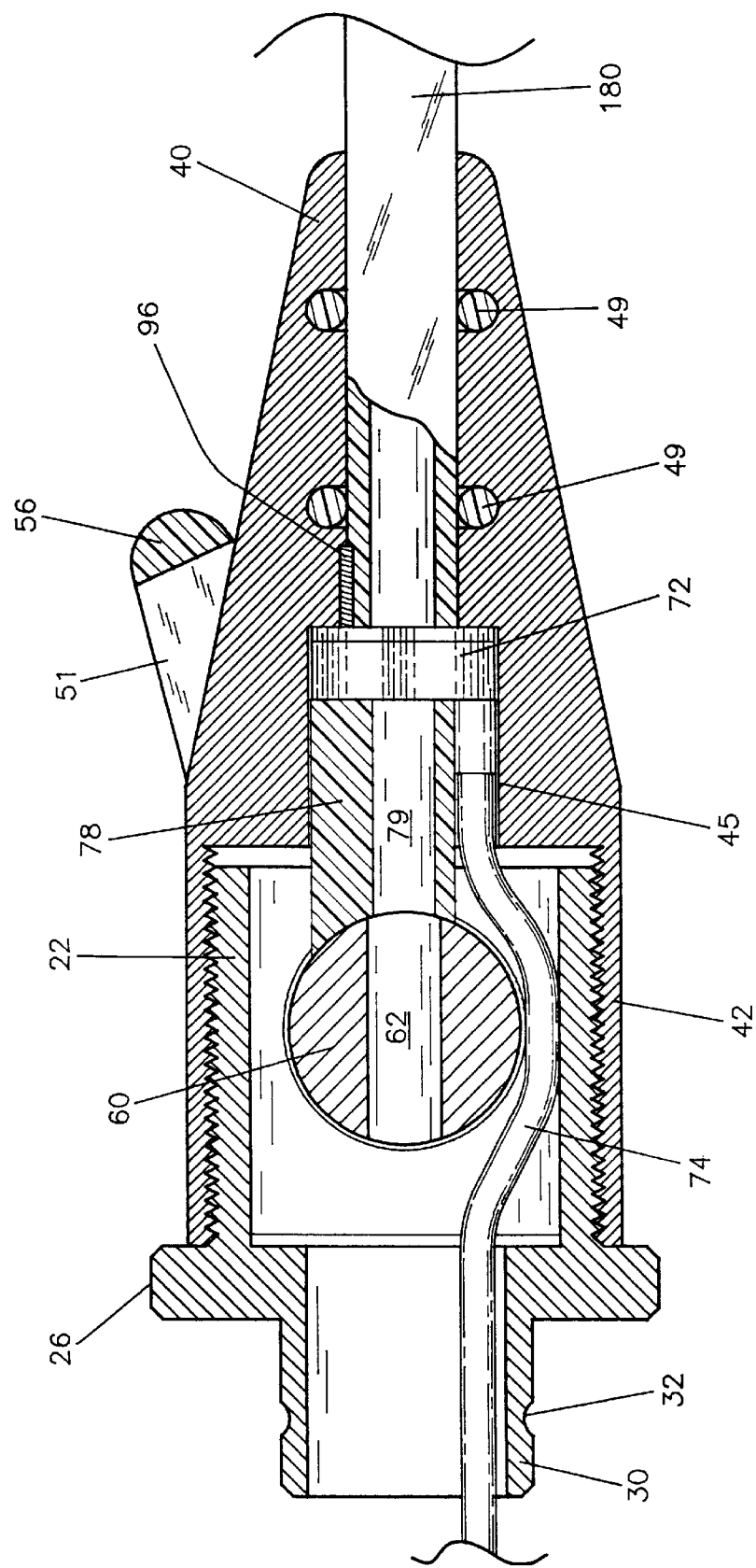
FIG. 8 is a cross sectional view of another modified dental suction tool with the suction valve in the open position.
Figure 9:
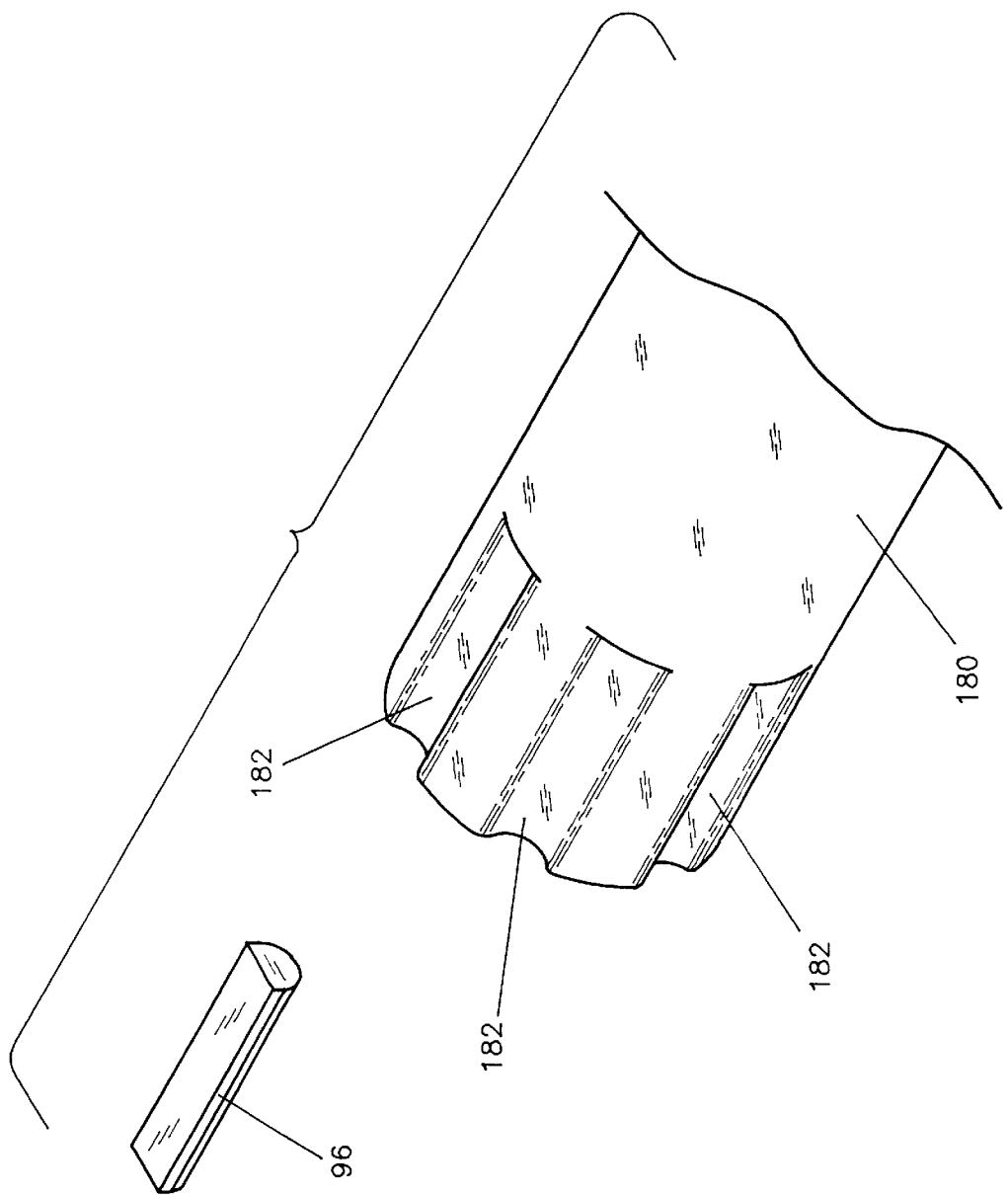
FIG. 9 is an isometric exploded view of a modified suction tip and its corresponding key element of the present invention.

FIGS. 7, 8 and 9 show another modification of the dental suction tool 10 of the present invention. Like reference numerals are used to identify the elements from FIGS. 1–3 that are the same in FIGS. 7 and 8.

In FIGS. 7, 8 and 9, a key 96 is added to the interior of the valve body 40 in front of the light ring 72. This key 96 will act as an alignment device when the suction tip 180 is inserted into the valve body 40.

As shown in FIGS. 7 and 9, the suction tip 180 has a plurality of recesses 182 that are positioned around the circumference of the suction tip 180 in the outer wall surface thereof in equally spaced locations. In the preferred embodiment of the present invention as shown in FIGS. 7 and 9, the recesses 182 are formed in the outer wall surface of the suction tip 180. When the suction tip 180 is inserted into the valve body 40, one of the recesses 182 aligns with the key 96 and effects the proper alignment of the suction tip 180 in the valve body 40. Since the suction tip 180 has a slight bend therein, by providing a plurality of recesses 182 around the circumference of the suction tip 180, a dentist may orient the suction tip 180 in a number of directions to permit the suction tip 180 to be utilized in any desired manner by the dentist.

FIG. 8 also shows another embodiment of the suction tip 180 which eliminates the fiberoptic layer on the inside of the suction tip. In this embodiment, a clear plastic material that is light transmitting is used for the suction tip 180. When the light ring 72 is activated, light emitting therefrom will travel through the body of the suction tip 180 and be emitted from the end thereof. This embodiment simplifies the manufacturing of the suction tip 180 and lowers its cost.

Figure 10:
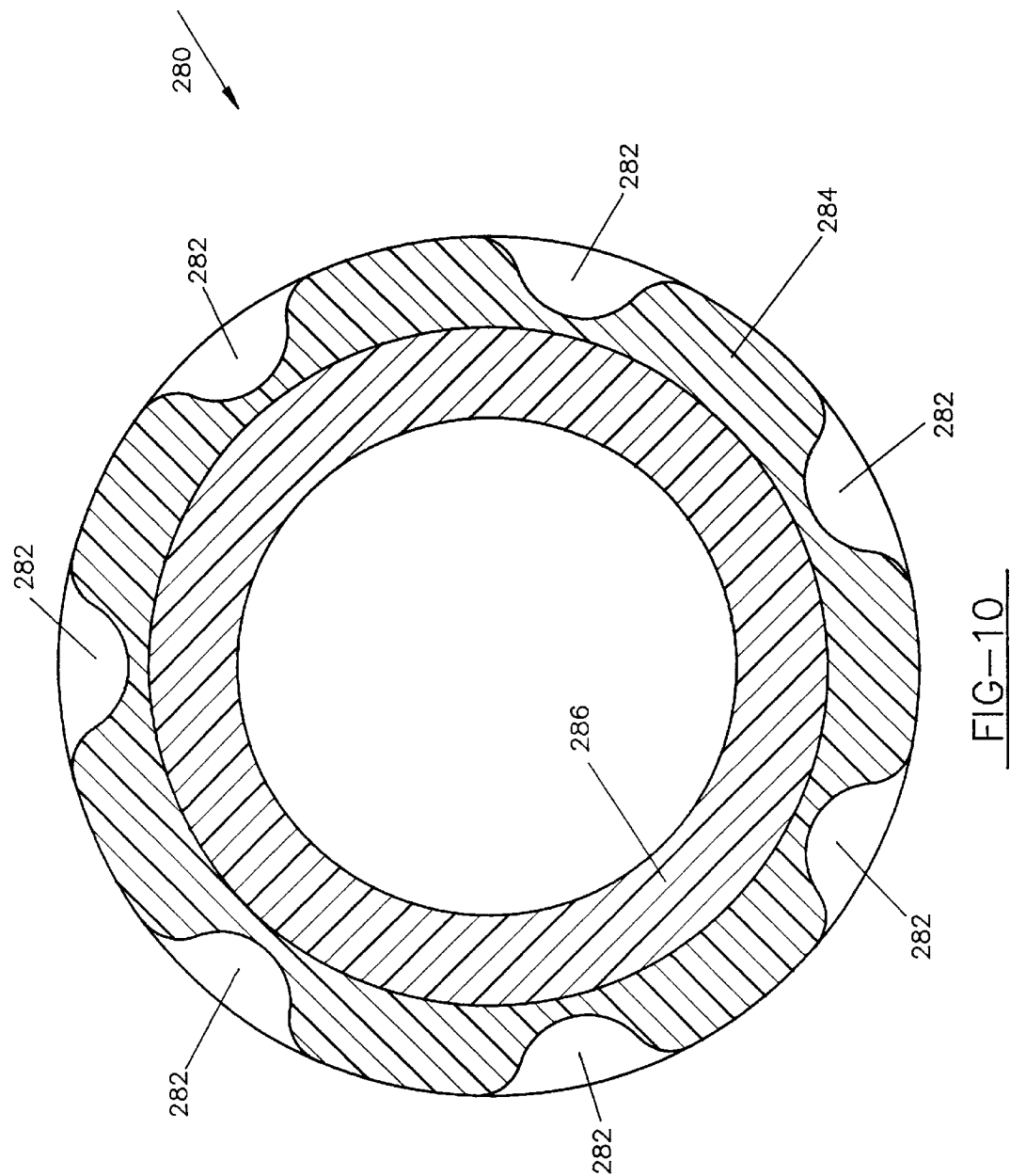
FIG. 10 shows an end view of still another modified suction tip of the present invention.
Figure 11:
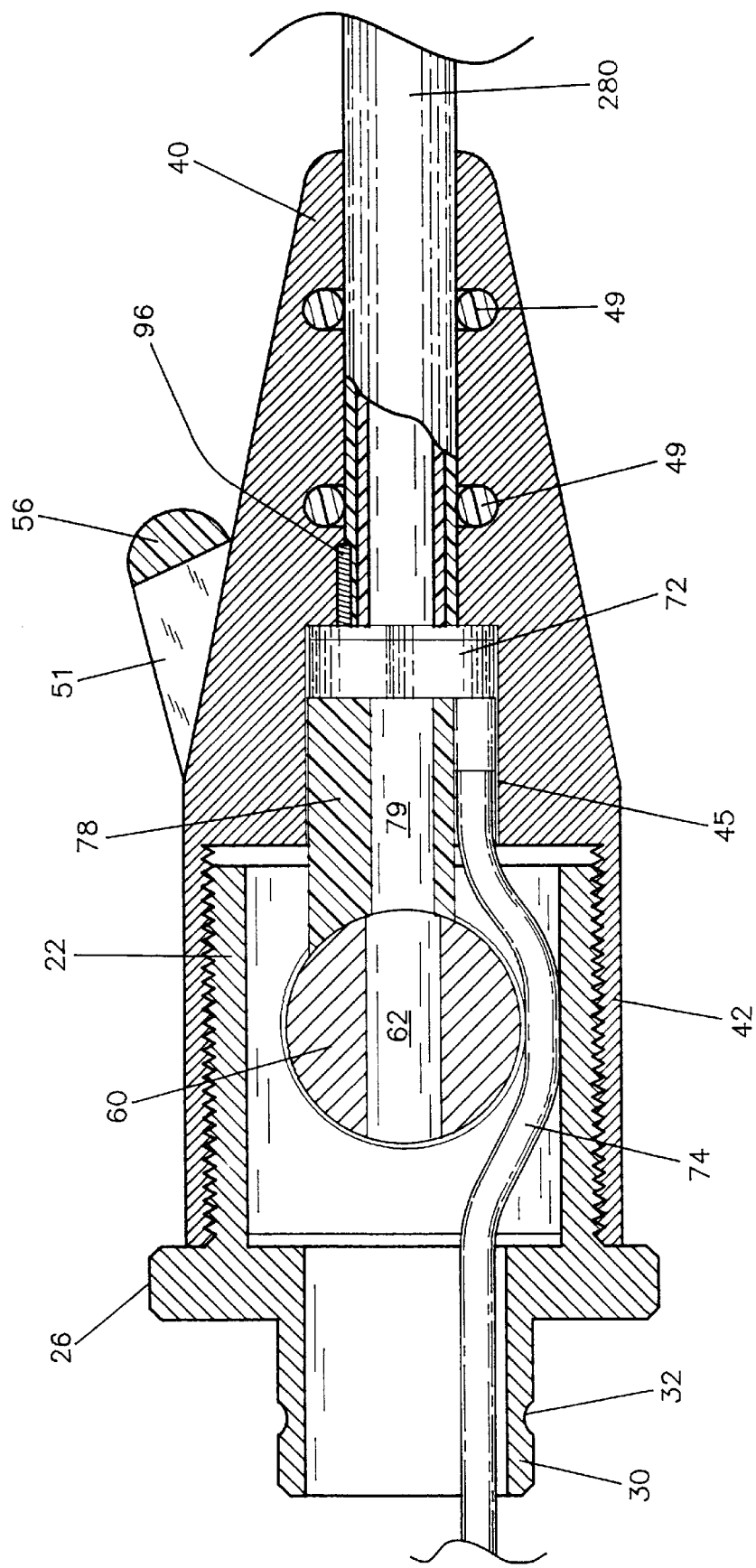
FIG. 11 is a cross sectional view of still another modified dental suction tool with the suction valve in the open position.

FIGS. 10 and 11 show still another modification of the dental suction tool 10 of the present invention. Like reference numerals are used to identify the elements from FIGS. 1–3 that are the same in FIG. 9 and FIG. 10.

The embodiment of the invention shown in FIG. 9 and FIG. 10 also use the key 96 that is added to the rear cavity 45 in front of the light ring 72. This key 96 will act as an alignment device when the suction tip 280 is inserted into the valve body 40.

The suction tip 280 also eliminates the fiberoptic layer on the inside of the suction tip. In this embodiment, the suction tip 280 is comprised of two extruded layers of plastic material, an outer layer 284 of opaque material and an inner layer 286 of clear plastic material that is light transmitting. The suction tip 280 has a plurality of recesses 282 that are positioned around the circumference of the suction tip 280 in the outer wall surface thereof in equally spaced locations. In the preferred embodiment of the present invention as shown in FIGS. 9 and 10, the recesses 282 are formed in the outer wall surface of the suction tip 280. When the light ring 72 is activated, light emitting therefrom will travel through the inner layers 286 of the suction tip 280 and be emitted from the end thereof. The outer layer 284 being opaque will prevent light loss through the lateral sides of the suction tip 280 so that the light intensity emitted from the end of the suction tip 280 is increased.

While the invention has been illustrated with respect to several specific embodiments thereof, these embodiments should be considered as illustrative rather than limiting. Various modifications and additions may be made and will be apparent to those skilled in the art. Accordingly, the invention should not be limited by the foregoing description, but rather should be defined only by the following claims.

What is claimed is:

1. A suction tip for use in a dental suction tool comprising a disposable plastic material formed as a generally cylindrical hollow tubing, one end of the suction tip having at least one beveled section formed in a circumferential portion of an outer wall surface of the suction tip so with the remainder of the suction tip being generally circular in cross section so that the suction tip can be properly aligned in the dental suction tool.

2. A suction tip for use in a dental suction tool comprising a plastic material formed as a generally cylindrical hollow tubing, one end of the suction tip having at least one generally U-shaped recess formed in a circumferential portion of an outer wall surface of the suction tip so that the suction Hip can be properly aligned in the dental suction tool.

3. The suction tip of claim 2 in which a plurality of the recesses are provided circumferentially around the perimeter of the suction tip.

4. The suction tip of claim 2 in which a plurality of the recesses are provided circumferentially and equally spaced around the perimeter of the suction tip.

5. The suction tip of claims 2 in which the suction tip comprises a single layer of light transmitting material.

6. A suction tip for use in a dental suction tool comprising a plastic material formed as a generally cylindrical hollow tubing, one end of the suction tip having at least one recess formed in an outer wall surface of the suction tip so that the suction tip can be properly aligned in the dental suction tool, the suction tip further comprising an inner layer of fiberoptic material and an outer layer of plastic material.

7. The suction tip of claim 6 in which a plurality of recesses are provided circumferentially around the perimeter of the suction tip.

8. The suction tip of claim 6 in which the outer layer is light transmitting material.

9. The suction tip of claim 6 in which the outer layer is opaque material.

10. A suction tip for use in a dental suction tool comprising a plastic material formed as a generally cylindrical hollow tubing, one end of the suction tip having at least one recess formed in an outer wall surface of the suction tip so that the suction tip can be properly aligned in the dental suction tool, the suction tip further comprising an inner layer of light transmitting material and an outer layer of opaque material.

11. A suction tip for use in a dental suction tool comprising a plastic material formed as a generally cylindrical hollow tubing, one end of the suction tip having two beveled sections provided on diametrically opposed sides of the suction tip so that the suction tip can be properly aligned in the dental suction tool.

12. The suction tip of claim 11 in which the suction tip comprises a single layer of light transmitting material.

13. A suction tip for use in a dental suction tool comprising a plastic material formed as a generally cylindrical hollow tubing, one end of the suction tip having at least one beveled section formed in an outer wall surface of the suction tip so that the suction tip can be properly aligned in the dental suction tool, the suction tip further comprising an inner layer of fiberoptic material and an outer layer of plastic material.

14. The suction tip of claim 13 in which the outer layer is light transmitting material.

15. The suction tip of claim 13 in which the outer layer is opaque material.

16. A suction tip for use in a dental suction tool comprising a plastic material formed as a generally cylindrical hollow tubing, one end of the suction tip having at least one beveled section formed in an outer wall surface of the suction tip so that the suction tip can be properly aligned in the dental suction tool, the suction tip further comprising an inner layer of light transmitting material and an outer layer of opaque material.

\* \* \* \* \*